US00PP11865P2

(12) United States Plant Patent
Clark et al.

(10) Patent No.: US PP11,865 P2
(45) Date of Patent: May 8, 2001

(54) BLACKBERRY PLANT NAMED 'APACHE'

(75) Inventors: John Reuben Clark; James Norman Moore, both of Fayetteville, AR (US)

(73) Assignee: University of Arkansas, Fayetteville, AR (US)

( * ) Notice: Subject to any disclaimer, the term of this patent is extended or adjusted under 35 U.S.C. 154(b) by 0 days.

(21) Appl. No.: 09/228,505

(22) Filed: Jan. 11, 1999

(51) Int. Cl.[7] ..... A01H 5/00
(52) U.S. Cl. ..... Plt./203

(58) Field of Search ..... Plt./203

*Primary Examiner*—Bruce R. Campell
*Assistant Examiner*—Anne Marie Grünberg

(57) ABSTRACT

Description and specifications of a new and distinct blackberry variety which originated from seed produced by a hand pollinated cross of Arkansas Selection 1007 (non-patented) and 'Navaho' (U.S. Plant Pat. No. 6,679) is provided. This new blackberry variety can be distinguished by its high fruit yields, large fruit size, erect thornless canes, late ripening, prolific fruiting row establishment, and good fruit quality.

3 Drawing Sheets

SUMMARY OF THE INVENTION

The new and distinct variety of blackberry originated from a hand pollinated cross of Arkansas Selection 1007 (non-patented)×'Navaho' (U.S. Plant Pat. No. 6,679) made in 1988 at the Arkansas Agricultural Experiment Station Fruit Substation at Clarksville, Ark.

Plants and fruit of this new variety differ phenotypically from its parents. The new variety is earlier ripening and possesses better fruit firmness, greater vigor, and better fruit flavor than the parent Arkansas Selection 1007, and is later ripening and more productive than the parent 'Navaho' (U.S. Plant Pat. No. 6,679). Fruit size of the new variety is larger than either parent, and it retains larger fruit size throughout the harvest season than either of the parent blackberries. Although blackberries (Rubus subgenus Rubus) are highly heterogeneous and outcrossing, and most clones contain genes from more than one species, the new variety and its progenitor lines phenotypically exhibit characters predominately of the erect eastern United States species, *Rubus allegheniensis* Porter (highbush blackberry) possibly introgressed with *R. argutus* Link. (tall blackberry). Its genes for thornlessness were derived frm the British cultivar 'Merton Thornless' (non-patented), a derivative of *Rubus ulmifolius* Schott.

The seeds resulting from this controlled hybridization were germinated in a greenhouse in the spring of 1989 and planted in a field on the Arkansas Agricultural Experiment Station in Clarksville, Ark. The seedlings fruited during the summer of 1991 and one, designated Ark. 1798, was selected for its very large fruit size, erect plant growth habit, thornless canes, and good fruit quality.

During 1991, the original plant selection was propagated asexually from root cuttings, at the above noted location, and a test row of 20 plants was established. Subsequently, larger test plantings have been established with asexually multiplied plants at three locations in Arkansas.

The new variety has been asexually multiplied annually since 1991 by the use of root cuttings and by rooting softwood cuttings. It forms new plants from adventitious buds on root cutting more readily than its parent 'Navaho' (U.S. Plant Pat. No. 6,679). During all asexual multiplication, the characteristics of the original plant have been maintained and no aberrant phenotypes have appeared.

Test plantings over a wide geographic area have shown this new variety to be adapted to differing soil and climatic conditions.

Plants of the new variety are vigorous and prolific and row establishment following planting is more rapid than with other thornless varieties. Both primocanes and floricanes are erect in growth habit, and self-supporting, requiring no trellis support. The plants are genetically thornless, having the recessive genes for thornless derived from the variety 'Merton Thornless' (non-patented). Plants and fruit are moderately tolerant to anthracnose [*Elsinoe veneta* (Burkh.) Jenkins], and plants appear immune to orange rust [*Gymnoconia nitens* (Schwein.) F. Kern and H. W. Thurston.] The bloom period of the new variety averages two to three days earlier than the cultivar 'Navaho' (U.S. Plant Pat. No. 6,679).

Fruit of the new variety begins ripening five days later than the 'Navaho' (U.S. Plant Pat. No. 6,679) variety, but is more concentrated in ripening, with a fruiting period 10 days shorter than 'Navaho' (U.S. Plant Pat. No. 6,679). Average ripening date is June 15 in central Arkansas. The harvest period is concentrated, with ripening over nearly a 5 week period, in contrast to the 'Navaho' (U.S. Plant Pat. No. 6,679) variety which produces for six weeks. Fruit yields of the new variety are usually 5 to 7 lb/plant and are significantly higher than the 'Navaho' (U.S. Plant Pat. No. 6,679) variety (with yields of 3 to 4 lb/plant) at all test locations and are comparable to the high yielding 'Shawnee' (U.S. Plant Pat. No. 5,686) variety (5 to 7 lb/plant). Yields are consistent from year to year.

The fruit is blocky-conical in shape, bright glossy black in color and very attractive. The fruit is large (8–10 g) and twice the size of the 'Navaho' (U.S. Plant Pat. No. 6,679) variety. Fruit size of the new variety is maintained well throughout the entire harvest season. The new variety exhibits excellent fruit fertility with full drupelet set in contrast to 'Navaho' (U.S. Plant Pat. No. 6,679), which has some drupelet sterility. The fruit is moderately firm at maturity, rating more firm than the 'Shawnee' (U.S. Plant Pat. No. 5,686) and 'Choctaw' (U.S. Plant Pat. No. 6,678) varieties, but less firm than the 'Navaho' (U.S. Plant Pat. No. 6,679)

variety. Storage ability of fresh fruit of the new variety is superior to both the 'Shawnee' (U.S. Plant Pat. No. 5,686) and 'Choctaw' (U.S. Plant Pat. No. 6,678) varieties in that fruit firmness is superior to these varieties and resulting storage period is longer, but storage ability of the new variety is less than the 'Navaho' (U.S. Plant Pat. No. 6,679) variety.

The fresh fruit rates good in flavor, being superior to the 'Shawnee' (U.S. Plant Pat. No. 5,686) variety, but less flavorful than the 'Navaho' (U.S. Plant Pat. No. 6,679) variety. The flavor is sweet and mildly subacid, with a distinct blackberry aroma. Flavor is sweeter and more aromatic than the 'Shawnee' (U.S. Plant Pat. No. 5,686) variety. The soluble solids concentration averages 10.7%, which is higher than most other blackberry varieties, but slightly less than 'Navaho' (U.S. Plant Pat. No. 6,679) (11.4%). Dry seed weight averages 4.8 mg/seed, and seeds are larger than those of the 'Navaho' (U.S. Plant Pat. No. 6,679) variety.

Fruit clusters are medium-large, cymose, and are mostly borne on the periphery of the plant canopy, providing easy access to harvest. Flower fertility is high and clusters are well filled.

The new variety has been named the 'APACHE' cultivar.

BRIEF DESCRIPTION OF THE PHOTOGRAPHS

The accompanying photographs show typical specimens of the fruit, leaf and canes of the new variety in color as nearly true as it is reasonably possible to make in a color illustration of this character.

DETAILED DESCRIPTION OF THE NEW VARIETY

The following is a detailed description of the botanical and pomological characteristics of the subject blackberry. Color data are presented in Royal Horticultural Society Colour Chart designations and are supplemented with readings from a Minolta Chroma Meter CR-200, version 3.0, which measures absolute chromaticity in tristimulus values Y, x, and y as determined by the Commission Internationale de l'Eclairage (CIE Yxy). Calibration was performed using a standard white plate supplied by the manufacturer.

Where dimensions, sizes, colors and other characteristics are given, it is to be understood that such characteristics are approximations of averages set forth as accurately as practicable.

The descriptions reported herein are from specimens grown at Clarksville, Arkansas unless otherwise noted.

Plant:

*Size.*—Medium, erect.

*Growth habit.*—Vigorous, prolific suckering from crowns, good suckering from roots, canes erect.

*Growth rate.*—Primocanes reach tipping height (107 cm) in 59 days from emergence.

*Productivity.*—High and for duration of five weeks; consistent from year to year. Yields consistently range from 5 to 7 lb/plant, exceeding 'Navaho' (U.S. Plant Pat. No. 6,679) (with yields of 3–4 lb/plant).

*Cold hardiness.*—Hardy to −20° C., similar to 'Navaho' (U.S. Plant Pat. No. 6,679).

*Canes.*—Thornless, erect. Cane diameter: base 1.22 cm, midpoint 1.10 cm, terminal 0.90 cm. Internode length: base 9.60 cm, midpoint 9.23 cm, terminal 7.13 cm. Floricane (winter cane) color: base-Yellow Green Group (148A) Y=6.62, x=0.3723, y=0.3468; midpoint-Yellow Green Group (152A) Y=8.21, x=0.3856, y=0.3723; terminus — Yellow Green Group (152B)Y=8.21, x=0.3841, y=0.3683. Primocane color: base-Yellow Green Group (146C) Y=15.67, x=3653, y=0.4151; midpoint-Yellow Green Group (146D) Y=14.98, x=0.3628, y=0.4185; terminus-Yellow Green Group (146B) Y=13.34, x=0.3647, y=0.4288. Date of primocane emergence; Julian 103.

*Disease resistance.*—Moderate to anthracnose; immune to orange rust.

Foliage:

*Primocane.*—Leaves — Large. Mature compound leaf width 8.84 cm; length 11.69 cm. Leaflet: Width 6.5 cm; length 9.1 cm; shape roundish to ovate with acuminate to acute apex and subcordate base; margin serrate; light pubescence on both abaxial and adaxial surfaces. Number of leaflets per compound leaf: 3 to 5. Color: Base abaxial-Green Group (138A) Y=14.04, x=0.3364, y=0.3944; adaxial-Yellow Green Group (147A) Y=7.91, x=0.3287, y=0.3956; midpoint abaxial- Green Group (137C) Y=16.66, x=0.3389, y=0.4002; adaxial-Green Group (137A) Y=8.60, x=0.3325, y=0.4071; terminal abaxial-Green Group (137C) Y=17.82, x=0.3436, y=0.4067; adaxial-Green Group (137A) Y=9.79, x=0.3394, y=0.4150. Petioles — Length: 4.7 cm. Color: Yellow Green Group (146C). Petioules — Length: 2.4 cm. Color: Yellow Green Group (146D). Stipules — Length: 0.9 cm. Width: 0.2 cm.

*Floricane.*—Leaves — Large. Mature compound leaf width 10.6 cm; length 8.8 cm. Leaflet: width 3.7 cm; length 5.2 cm; shape ovate, with acuminate to acute apex and obtuse base; margin serrate; light pubescence on both abaxial and adaxial surface. Number of leaflets per compound leaf: 3 to 5. Color: base abaxial-Yellow Green Group (147B)Y=15.11, X=0.3382, y=0.3952; adaxial-Green Group (139A) Y=8.46, x=0.3292, y=0.3927; midpoint abaxial-Green Group (138A) Y=14.40, x=0.3355, y=0.3919; adaxial-Yellow Green Group (147A) Y=7.73, x=0.3265, y=0.3897; terminal abaxial-Green Group (137C) Y=14.66,x=0.3362,y=0.3935; adaxial-Green Group (137A)Y=7.92, x=0.3292, y=3923. Petioles — Length: 2.7 cm. Color: Yellow Green Group (146C). Petioules — Length 0.34 cm. Color: Yellow Green Group (147C). Stipules — Length: 1.1 cm. Width: 0.3 cm.

Flowers:

*Date of bloom.*—First — Julian 130; 50% — Julian 136; Last — Julian 143.

*Blossom color.*—Purple Group (75D) Y=63.73, x=0.3318, y=0.3245.

*Reproductive organs.*—Stamens — erect, numerous. Pistils — numerous. Pollen — normal and abundant.

*Flower diameter.*—3.6 cm.

*Petal size.*—Length: 1.7 cm. Width: 1.4 cm.

*Number flowers per cluster.*—4 to 6.

*Number of petals per flower.*—5.

*Number of sepals per flower.*—5.

*Peduncle length.*—2.11 cm.

*Peduncle color.*—Green Group (143C).

*Cyme type.*—Elongate simple cyme.

Fruit:

*Maturity.*—Late, 5 days after 'Navaho' (U.S. Plant Pat. No. 6,679). Average first ripe date is June 20. Average period of ripening is June 20 to July 27.

*Size.*—Large, average 8.5 g, uniform. Diameter: Fruit at primary position on inflorescence: equator 2.48 cm, base pole 2.06 cm, terminal pole 1.55 cm; fruit at secondary positions on inflorescence: equator 2.48 cm., base pole 1.89 cm, terminal pole 1.58 cm. Length (Primary fruit) 3.7 cm.

*Shape.*—Blocky-conical, uniform.

*Color.*—Glossy black; Black Group (202A) Y=3.19, x=0.3123, y=0.3161.

*Drupelet size.*—Medium, 5.9 mm.

*Seed size.*—Medium, 4.8 mg (dry wt.).

*Soluble solids.*—10.7%.

*pH.*—3.30 (as measured by pH meter on undiluted juice from a sample of 25 fully-ripe berries).

*Acidity.*—0.89 g tartaric acid/100 ml.

*Processed quality.*—Good, similar to 'Arapaho' (U.S. Plant Pat. No. 8,510), superior to 'Shawnee' (U.S. Plant Pat. No. 5,686).

*Uses.*—Fresh and processed, jellies, jams, juice, wine.

The variety: The most distinctive features of the variety are its high yields, large fruit size, late ripening, erect thornless canes, prolific fruiting row establishment, and good fruit quality.

We claim:

1. A new and distinct variety of blackberry plant, substantially as illustrated and described, characterized by its high yields, large fruit size, erect thornless canes, late ripening, prolific fruiting row establishment, and good fruit quality.

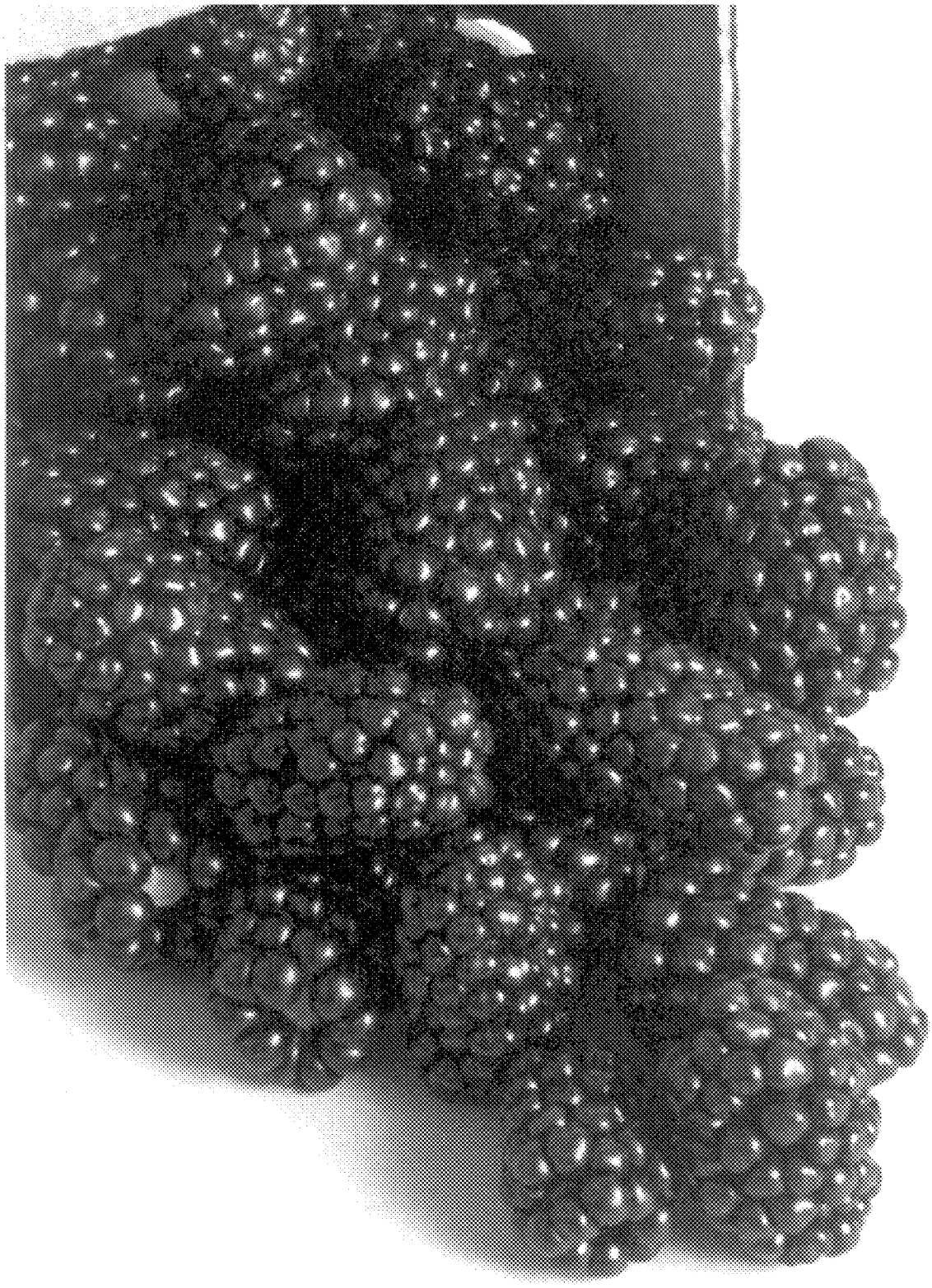

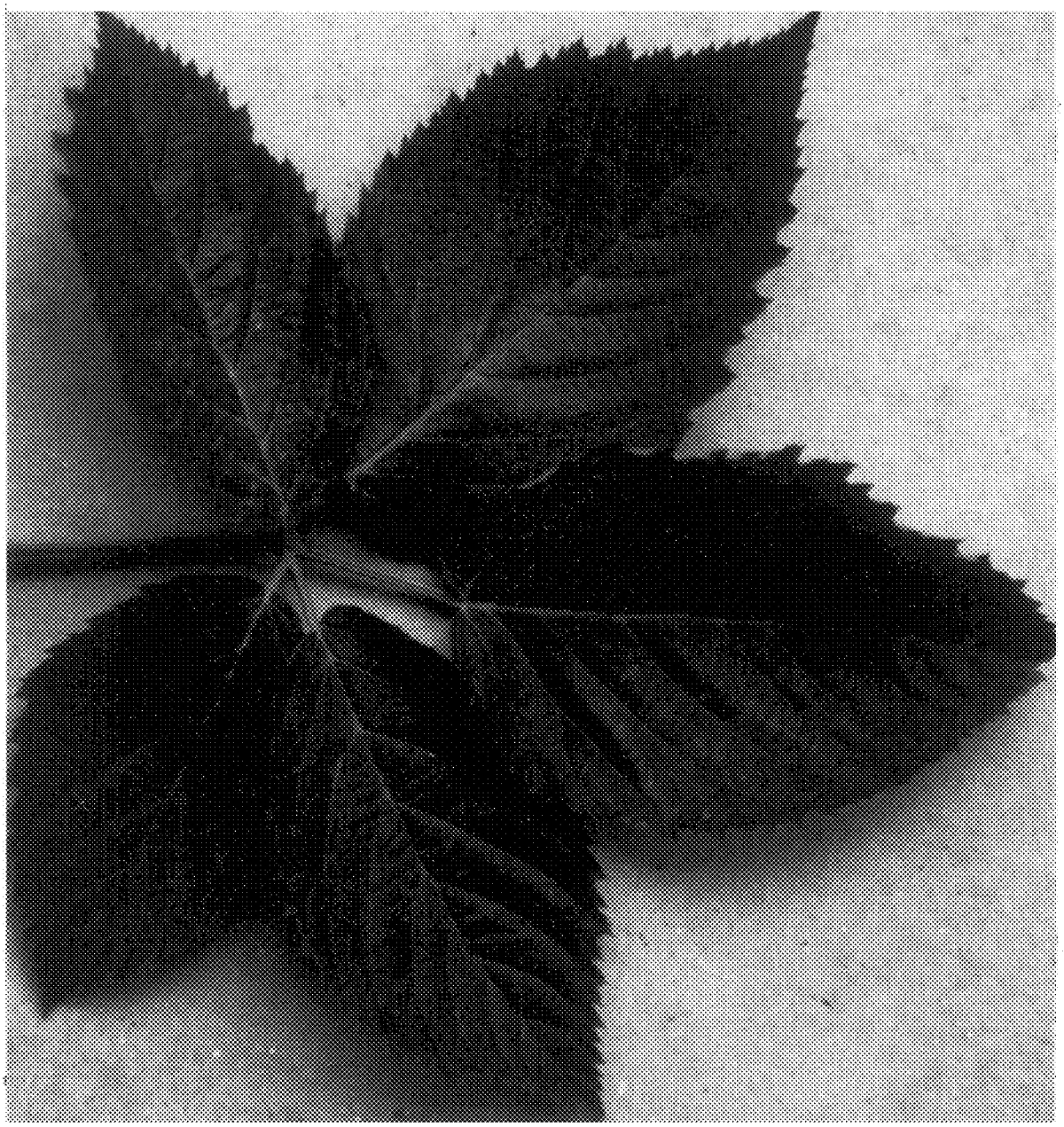

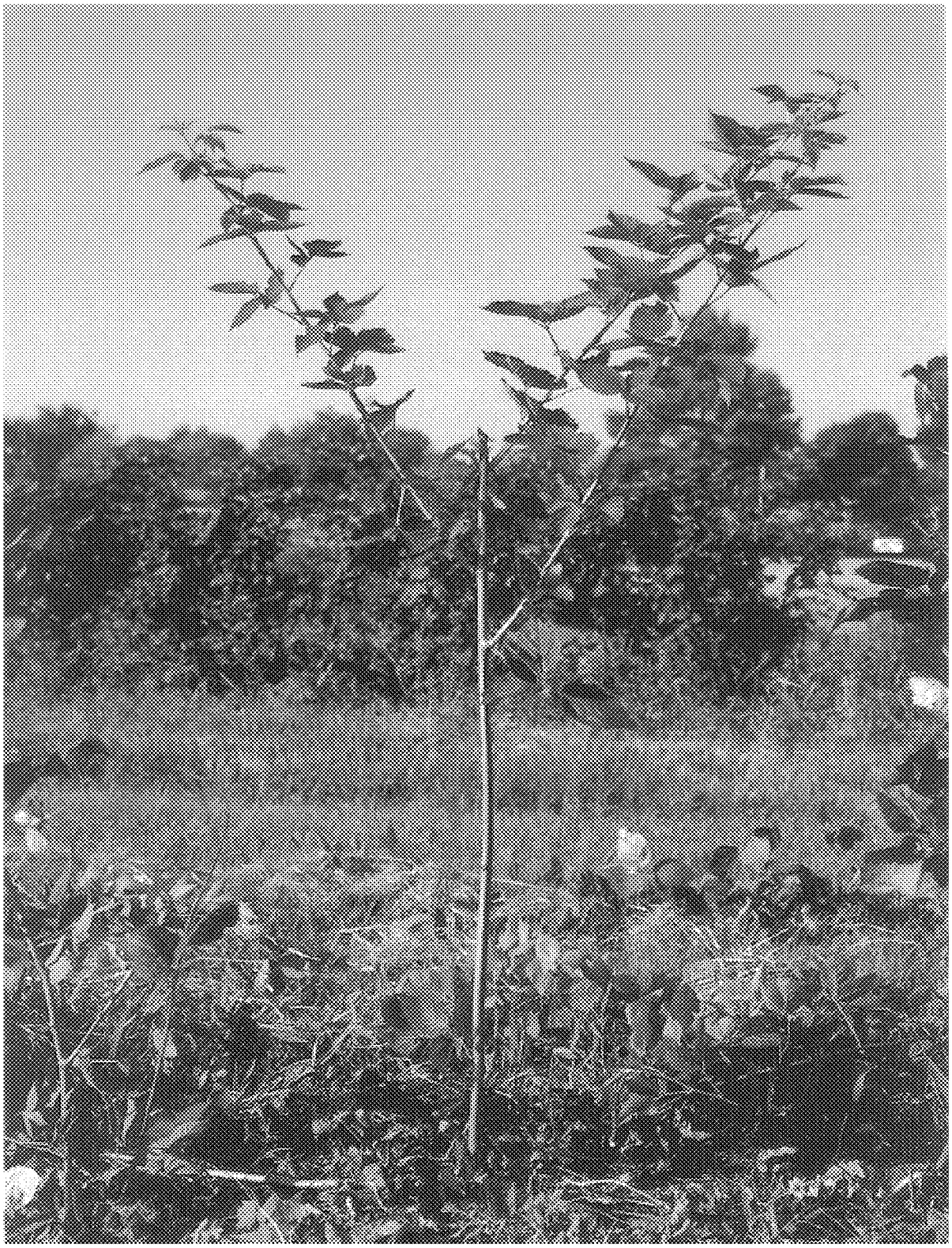

* * * * *